US010300045B2

(12) United States Patent
da Rocha et al.

(10) Patent No.: US 10,300,045 B2
(45) Date of Patent: May 28, 2019

(54) DELAYED RELEASE FEED-THROUGH VETERINARY COMPOSITIONS WITH OVICIDAL AND LARVICIDAL ACTIVITY AGAINST SUSCEPTIBLE AND RESISTANT STRAINS OF PARASITES IN RUMINANTS' FECES, USE OF THESE COMPOSITIONS, METHOD FOR DELAYING THE RELEASE OF THESE COMPOSITIONS

(71) Applicant: Champion USA LLC, Delray Beach, FL (US)

(72) Inventors: Flavia Sette da Rocha, San Paulo (BR); Flavio Alves da Rocha, Delray Beach, FL (US)

(73) Assignee: Champion USA LLC, Delray Beach, FL (US)

( * ) Notice: Subject to any disclaimer, the term of this patent is extended or adjusted under 35 U.S.C. 154(b) by 0 days.

(21) Appl. No.: 15/823,965

(22) Filed: Nov. 28, 2017

(65) Prior Publication Data
US 2018/0333393 A1 Nov. 22, 2018

(30) Foreign Application Priority Data

May 19, 2017 (BR) .......................... 10 2017 010598

(51) Int. Cl.
| | |
|---|---|
| *A61K 31/4184* | (2006.01) |
| *A61K 47/32* | (2006.01) |
| *A61K 47/38* | (2006.01) |
| *A23K 20/137* | (2016.01) |
| *A23K 20/147* | (2016.01) |
| *A23K 20/174* | (2016.01) |
| *A23K 20/26* | (2016.01) |
| *A23K 20/22* | (2016.01) |
| *A61K 47/42* | (2017.01) |
| *A61K 9/00* | (2006.01) |
| *A23K 50/10* | (2016.01) |
| *A23K 40/10* | (2016.01) |

(52) U.S. Cl.
CPC ........ *A61K 31/4184* (2013.01); *A23K 20/137* (2016.05); *A23K 20/147* (2016.05); *A23K 20/174* (2016.05); *A23K 20/22* (2016.05); *A23K 20/26* (2016.05); *A23K 40/10* (2016.05); *A23K 50/10* (2016.05); *A61K 9/0002* (2013.01); *A61K 47/32* (2013.01); *A61K 47/38* (2013.01); *A61K 47/42* (2013.01)

(58) Field of Classification Search
CPC .............. A61K 31/4184; A23K 20/137; A23K 20/147; A23K 20/174; A23K 20/22; A23K 20/26
USPC ........................................................ 514/394
See application file for complete search history.

(56) References Cited

U.S. PATENT DOCUMENTS

| | | | | |
|---|---|---|---|---|
| 3,401,171 A | * | 9/1968 | Craig ................... | C07D 235/30 548/307.4 |
| 2007/0053943 A1 | | 3/2007 | Wang et al. | |
| 2016/0051524 A1 | * | 2/2016 | de Rose ............... | A61K 31/415 514/30 |

FOREIGN PATENT DOCUMENTS

| | | | |
|---|---|---|---|
| EP | 2468096 A1 | 6/2012 | |
| WO | 2014100403 A1 | 6/2014 | |
| WO | WO-2014169092 A1 * | 10/2014 | ......... A61K 31/7048 |

OTHER PUBLICATIONS

Amarante, "Anti-helminticos. In: Os parasitas de ovinos [online]," San Paulo: Editora UNESP, 2014, pp. 123-136.
Amarante et al., "Efeito da Administracao de Oxfendazol, Ivermectina e Levamisol Sobre os Exames Coproparasitologicos de Ovinos," San Paulo, vol. 29, No. 1, 1992, pp. 31-38.
Anziani et al., "Resistance to benzimidazole and macrocyclic lactone anthelmintics in cattle nematodes in Argentina," Veterinary Parasitology, vol. 122, 2004, pp. 303-306.
Bassetto, "Protecao de Ovinos e Bovinos Contra Haemonchose Apos Imunizacao com Antigenos Oriundos da Membrana Intestinal de Haemonchus contortus" Universidade Estadual Paulista, 2015 (English translation attached).
Bowie, "Alternative Treatments for Haemonchus Contortus in Sheep: Testing of a Natural Dewormer and Literature Review of Management Methods," Dickinson College Honors Theses, 2014, Paper 163.
Cezar et al., "Acao anti-helmintica de diferentes formulacoes de lactonas macrociclicas em cepas resistentes de nematodeos de bovinos" Pesq. Vet. Bras., vol. 30, No. 7, 2010, pp. 523-528 (with English abstract).
Condi et al., "Moxidectin-resistant nematodes in cattle in Brazil," Veterinary Parasitology, vol. 161, 2009, pp. 213-217.
Da Cruz et al., "Anthelmintic efficacy and management practices in sheep farms from the state of Rio de Janeiro Brazil," Veterinary Parasitology, vol. 170, 2010, pp. 340-343.
Das Neves, "Diagnostico de Resistencia Anti-Helmintica em Bovinos," Universidade Estadual Paulista Julio de Mesquita Filho Faculdade de Medicina Veterinaria e Zootecnia, 2014 (English translation attached).
Edmonds et al., "Anthelmintic resistance of Ostertagia ostertagi and Cooperia oncophora to macrocyclic lactones in cattle from the western United States," Veterinary Parasitology, vol. 170, 2010, pp. 224-229.
Fiel et al., "Resistance of Cooperia to ivermectin treatments in grazing cattle of the Humid Pampa, Argentina," Veterinary Parasitology, vol. 2059, 2001, pp. 1-7.
Gasbarre et al., "Further characterization of a cattle nematode population with demonstrated resistance to current anthelmintics," Veterinary Parasitology, vol. 166, 2009, pp. 275-280.

(Continued)

Primary Examiner — Yong L Chu
(74) Attorney, Agent, or Firm — Kilyk & Bowersox, P.L.L.C.

(57) ABSTRACT

A veterinary composition is disclosed and is based on anthelmintic compounds, particularly from the benzimidazole group, with delayed release properties, preferably in the form of granules or pellets, to be added to feed or feed supplements offered to ruminants in order to control eggs and larvae of helminths, preferably from the genus *Haemonchus* spp.

14 Claims, No Drawings

(56) References Cited

OTHER PUBLICATIONS

Geary et al., "The changing landscape of antiparasitic drug discovery for veterinary medicine," Trends in Parasitology, vol. 20, No. 10, 2004, pp. 449-455.

Howell et al., "Prevalence of anthelmintic resistance on sheep and goat farms in the southeastern United States," JAVMA, vol. 233, No. 12, 2008, pp. 1913-1919.

Humbert et al., "Molecular approaches to studying benzimidazole resistance in trichostrongylid nematode parasites of small ruminants," Veterinary Parasitology, vol. 101, 2001, pp. 405-414.

Kaminsky et al., "Identification of the amino-acetonitrile derivative monepantel (AAD 1566) as a new anthelmintic drug development candidate," Parasitol Res, vol. 103, 2008, pp. 931-939.

Kaplan, "Drug resistance in nematodes of veterinary importance: a status report," Trends in Parasitology, vol. 20, No. 10, 2004, pp. 477-481.

Kaplan et al., "Prevalence of anthelmintic resistant cyathostomes on horse farms," JAVMA, vol. 225, No. 6, 2004, pp. 903-910.

Leite-Browning, "Causes of Infectious Abortions in Goats," Alabama Cooperative Extension System, 2006, pp. 1-8.

Little et al., Field efficacy and safety of an oral formulation of the novel combination anthelmintic, derquantel-abamectin, in sheep in New Zealand, New Zealand Veterinary Journal, vol. 58, No. 3, 2010, pp. 121-129.

Mejia et al., "Multispecies and multiple anthelmintic resistance on cattle nematodes in a farm in Argentina: the beginning of high resistance?," Vet. Res., vol. 34, 2003, pp. 461-467.

Mena et al., "First report in Mexico on ivermectin resistance on naturally infected calves with gastrointestinal nematodes," Vet. Méx., vol. 39, No. 4, 2008 (English translation attached).

Molento, "Resistencia de Helmintos em Ovinos e Caprinos," Rev. Bras. Parasitol. Vet., vol. 13, No. 1, 2004, pp. 82-87.

Molento et al., "Influence of verapamil on the pharmacokinetics of the antiparasitic drugs ivermectin and moxidectin in sheep," Parasitol Res., vol. 92, 2004, pp. 121-127.

Da Costa, Comportamento e Bem-Estar de Bovinos e Suas Relacoes corn a Producao de Qualidade, Adaptado de Panahos da Costa e Pinto, 2003, pp. 1-10.

Santos et al., "Helminth fauna of bovines from the Central-Western region, Minas Gerais State, Brazil" Ciencia Rural, vol. 40, No. 4, 2010, pp. 934-938.

Soutello et al., "Anthelmintic resistance in cattle nematodes in northwestern Sao Paulo State, Brazil," Veterinary Parasitology, vol. 148, 2007, pp. 360-364.

Von Samson-Himmelstjerna et al., "Effects of worm control practices examined by a combined faecal egg count and questionnaire survey on horse farms in Germany, Italy and the UK," Parasites & Vectors, 2009, pp. 1-7.

Waghorn et al., "Prevalence of anthelimintic resistance on sheep farms in New Zealand," New Zealand veterinary journal, 2006, pp. 271-277.

Suarez et al., "Anthelmintic resistance in cattle nematode in the western Pampeana Region of Argentina," Veterinary Parasitology, vol. 144, 2007, pp. 111-117.

International Search Report and Written Opinion issued in corresponding International Patent Application No. PCT/US2018/029492 dated Jul. 16, 2018 (10 pages).

* cited by examiner

DELAYED RELEASE FEED-THROUGH VETERINARY COMPOSITIONS WITH OVICIDAL AND LARVICIDAL ACTIVITY AGAINST SUSCEPTIBLE AND RESISTANT STRAINS OF PARASITES IN RUMINANTS' FECES, USE OF THESE COMPOSITIONS, METHOD FOR DELAYING THE RELEASE OF THESE COMPOSITIONS

FIELD OF INVENTION

The present invention regards a veterinary composition, to be mixed with animal feed or salt, preferably in the form of granules or pellets, based on anthelmintic compounds, particularly from the benzimidazole group, with delayed release properties, to control eggs and larvae of helminths, preferably from the genus *Haemonchus* spp., in ruminants' feces.

The blood sucking nematodes of *Haemonchus* genus are probably the most economically important parasites in ruminants raised in warm damp climates of tropics and sub tropics (BASSETTO, 2015). Also known as red stomach worms, wire worms or barber's pole worms, their incidence and pathology is well known in cattle (SANTOS, 2010; AMARANTE, 2011), goats (LEITE-BROWNING, 2006) and sheep (BOWIE, 2014). As with many other endoparasites, *Haemonchus* spp. show elevated resistance to traditional anthelmintics (DAS NEVES, 2014; BASSETTO, 2015).

The life cycle of gastrointestinal nematodes (among which figures *Haemonchus* spp.) comprises two different phases: a parasitic phase and a nonparasitic or free-living phase. The free-living phase begins after egg shedding among the host's feces—a single adult female *Haemonchus* can release between 5,000 and 10,000 eggs per day. Pastured animals will infect themselves by grazing on contaminated grass. The more animals are grazing in the same area, the higher the chance of worms to spread themselves among the herd.

After egg shedding, eggs develop in moist conditions in the feces and continue to develop into the L1 (rhabditiform) and L2 juvenile stages by feeding on bacteria in the dung. The L2 rhabditiform sheds its cuticle and then develops into the L3 filiariform infective larvae. Under favorable conditions of temperature and humidity, the period between egg shedding and the presence of the first infective larvae (L3) is 5-7 days. Infective larvae have a protective cuticle that helps them withstand heat and avoid desiccation for some time. They will crawl up blades of wet grass and wait to be ingested by a grazing animal. Sheep, goats and cattle become infected when they graze and eat contaminated grass. Infective larvae (L3) pass through the ruminants' digestive tract until they reach the abomasum (fourth, or 'true', stomach). The larvae will then shed their cuticle and burrow into the internal layer of the abomasum where they develop into L4, usually within 48 hours. In the final stage, L4 larvae molt and develop into the adult form (L5). The male and female adults mate and live in the abomasum, where they feed upon the host's blood and copulate.

The pre-patent period, i.e., the period of time between infective larvae ingestion by the host and the appearance of the first eggs among the host's feces is 21-28 days (*Haemonchus contortus*) and 28 days (*Haemonchus placei*). Similar life cycles and pre-patent periods are present in the vast majority of gastrointestinal nematodes that parasitizes ruminants.

The nematode piercing the abomasum causes a number of significant complications in the infected ruminants that can lead to death. The infected animals can display severe dehydration, diarrhea, unthrifty appearance, lethargy, depressed low energy behavior, rough hair coat and uncoordinated movements. Furthermore, significantly reduced growth and poor reproductive performance have been observed. The accumulation of fluid in the abdomen, gut wall, thoracic cavity and submandibular tissue—a phenomenon commonly called "bottle jaw", also is a common association with this infection. Severe blood loss, white mucous membranes, and anemia/low PCV are common complications of the infection.

The infection, called haemonchosis, causes large economic losses for farmers around the world, especially for those living in the warmer climates. Anthelmintics have been used in order to control these and other worm infections for a long time, but anthelmintic resistance among parasites is rapidly growing.

According to HOSSETTO (2000), dairy cattle with high incidence of worms can show a substantial loss in milk yield, up to 25% of the daily production. A 5%-10% raise in the annual mortality rate may be expected (Marques, 2003), especially among calves, as well as 12% less births per year (FADIL, n/a.).

Existing anthelmintics work by killing the adult forms and immature species by means of its toxic effect, although they don't possess enough residual power that leads to re-infestation cycle elimination. So, after 28-35 days an estimated 70% of worm infestation will be back. Moreover, existing anthelmintics leave toxic residues on beef and milk of the treated animals, and are more likely to be affected by anthelminthic resistance.

Parasitic resistance to anthelmintics is a phenomenon whereby members of a population are selected and become dominant after constant use of a chemical compound. The diagnosis will be positive for "resistance" when a certain drug that used to show 99% efficacy over the parasite burden reduction starts showing less than 95% efficacy against the same parasites after certain period of time (MOLENTO, 2004).

In recent years, the problem of anthelmintic resistance has reached new heights where it can no longer be ignored as a major issue in the control of parasites of livestock. It is an inconvenient truth that reports of resistance are no longer noteworthy; anthelmintic resistance is the status quo. In many parts of the world, multiple-resistant parasites are highly prevalent, and it is no longer uncommon to find sheep or goat farms where resistance exists to all available anthelmintic drugs (Cezar et al., 2010; da Cruz et al., 2010; Howell et al., 2008). In general, levels and spectrum of anthelmintic resistance are less severe in parasites of horses and cattle, but the same problems exist and seem to be worsening (Kaplan, 2004; Kaplan et al., 2004; Soutello et al., 2007; Suarez and Cristel, 2007; Traversa et al., 2009; Waghorn et al., 2006a). Thus, in some regions, high levels of multiple-drug resistance threaten the health and productivity of these species as well.

Until the recent introduction of monepantel (Kaminsky et al., 2008) in New Zealand and the United Kingdom, there had not been a new class of anthelmintics delivered to the livestock market since ivermectin almost 30 years ago. This new drug and others, such as derquantel (Little et al., 2010), may offer a temporary reprieve from the problems created by mounting failures of older anthelmintics. However, the development of new anthelmintic drug classes is not likely to solve the problem of anthelmintic resistance. The great cost associated with the development of new drugs and the trends of reduced levels of investment into new animal drug research over the past few decades make it extremely unlikely that we are entering a new phase where a continuous supply of new anthelmintic compounds will follow (Geary et al., 2004).

Over the past decade there have been increasing numbers of reports of anthelmintic resistance in gastrointestinal nematodes of cattle worldwide, most of which concern resistance to the avermectin/milbemycin drugs (Anziani et al., 2001, 2004; Condi et al., 2009; Demeler et al., 2010; Edmonds et al., 2010; Familton et al., 2001; Fiel et al., 2001; Gasbarre et al., 2009; Mejia et al., 2003; Mena et al., 2008).

The most comprehensive studies investigating the prevalence of anthelmintic resistance in cattle parasites have been performed in New Zealand (Waghorn et al., 2006a) and in South America (Soutello et al., 2007; Suarez and Cristel, 2007). In all three studies, injectable avermectin/milbemycin products were used, with data indicating that resistance is becoming a very serious problem in these regions.

The predominant genera infecting these cattle were *Cooperia* spp. and *Haemonchus* spp. and both genera were consistently found associated with resistance. In addition, there was evidence on two farms for moxidectin-resistance in *Oesophagostomum* spp. Resistance in *Oesophagostomum* spp. was subsequently confirmed using FECRT combined with a controlled efficacy test (using injectable moxidectin) on a cattle farm in Brazil (Condi et al., 2009). An interesting observation in this study was that 98.5% of the *Cooperia* spp. females recovered at necropsy (14 days after treatment) from the control animals had eggs inside the uterus, as compared to only 48.2% of the females recovered from the moxidectin treated group (P<0.001). A temporary suppression of egg output by worms surviving moxidectin treatment has been reported previously in sheep (Sutherland et al., 1999). These data indicate that moxidectin treatment may cause a temporary suppression in egg output; suggesting that FECRT data from moxidectin (and other macrocyclic lactone drugs) should be interpreted with caution to avoid mis- or under-diagnosis of anthelmintic resistance. These data also suggest that 14 days may not be a sufficient interval following moxidectin treatment for post-treatment feces collection, and that 17-21 days may be preferred.

To apply any of these anti-parasite drugs it's necessary to gather the herd and lead them to the corral.

A roundup is an extremely laborious activity that involves many people and has a long duration. Essentially, the herding of animals to the corral leads to a disorganization of their activities (PARANHOS DA COSTA & NETO, 2003), animals cannot feed, are subjected to stress, and this can lead to weight loss up to 15 kg per animal per roundup (ARENALES, 2004). Stressful roundup activities also raise the risk of accidents, which may lead to bruised carcasses (PARANHOS DA COSTA et al., 2004).

Further, the existing anthelmintics are known to leave residues in beef and milk, being necessary to establish their withdrawal periods.

Commonly Used Deworming Products

| | | | Warnings and Withdrawals** | |
|---|---|---|---|---|
| Type | Trade Name | Active Ingredient | Dairy & Milk | Beef & Slaughter |
| Block | SafeGuard Cattle Block | Fenbendazole | Note 1 | 11 d |
| Drench | Prohibit | Levamisole | Note 1 | 48 h |
| | Synanthic 9.06% | Oxfendazole | Note 1 | 7 d |
| | Synanthic 22.5% | Oxfendazole | Note 1 | 7 d |
| | Panacur | Fenbendazole | 0 | 8 d |
| | SafeGuard | Fenbendazole | 0 | 8 d |
| | Valbazen | Albendazole | Note 1, 2 | 27 d (Note 2) |
| Feed additives | SafeGuard | Fenbendazole | 0 | 13 d |
| | Rumatel | Morantel Tartrate | 0 | 14 d |
| Injectable | Levamisol | Levamisole | Note 1 | 7 d |
| | Ivermectin Containing | Ivermectin | Note 1 | 35 d |
| | Ivomec Plus, Noromectin Plus | Ivermectin/ Clorsulon | Note 1 Note 3 | 49 d 35 d |
| | Dectomax | Doramectin | Note 1 | 21 d |
| | Cydectin | Moxidectin | | |
| Paste | Panacur | Fenbendazole | 0 | 8 d |
| | SafeGuard | Fenbendazole | 0 | 8 d |
| Pour-on | Ivermectin Containing Pouron | Ivermectin Eprinomectin | Note 1 0 | 48 d 0 |
| | Eprinex | Doramectin | Note 3 | 45 d |
| | Dectomax Pouron Cydectin Pouron | Moxidectin | 0 | 0 |
| Mineral | SafeGuard Mineral dewormer | Fenbendazole | 0 | 13 d |

*Local feed dealerships may independently market feed mixes and blocks containing additive products.
Note 1:
Not to be used on dairy cattle of breeding age.
Note 2:
Not to be used during the first 45 days of pregnancy or for 45 days after bull removal.
Note 3:
Safe in dairy heifers up to 20 months of age.
**Withdrawals are subject to change.

SUMMARY OF THE PRESENT INVENTION

The compositions of the present invention offer one or more advantages over common anthelmintics, including one or more of the following aspects:

1) By mixing said composition, in its granule or pelletized form, with salt, feed or any other nutritional supplement offered to cattle, one avoids: the inconvenient costs that arise from rounding up the cattle into the corral, stress on the cattle, food deprivation and/or lesions;

2) By utilizing delayed-release technology, the active ingredient is essentially deployed only in the feces, therefore avoiding residues on the animal's living tissues and milk; and/or 3) By having the activity of the composition released or concentrated in the feces, the active ingredient has nearly or about 100% of its potency employed against immature nematode forms (larvae and eggs) present in the dung pat, with in loco ovicide and larvicide action, avoiding future infections.

DETAILED DESCRIPTION OF THE PRESENT INVENTION

Different from the prior art, including commercial uses available in the literature, the present invention pertains in part to a composition, preferably a veterinary composition, and method of treatment. The composition preferably is in the form of granules or pellets. The composition can be added to animal feed, or salt or any other nutritional supplement offered to animals, such as ruminants. The composition is effective in controlling helminths' eggs and larvae, especially of the *Haemonchus* genus, present in the animal's feces.

Administration of the composition of the present invention through feed or feed supplements allows for feces expelled by treated animals to contain the benzimidazole-based composition.

Benzimidazoles, the active ingredient, are a class of heterocyclic aromatic organic compounds that include a fusion of benzene and imidazole, as in the formula below:

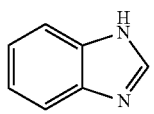

(I)

The benzimidazoles are characterized by a broad spectrum of activity against roundworms (nematodes), an ovicidal effect, and a wide safety margin. Examples of the benzimidazole compounds or benzimidazole drugs are: mebendazole, flubendazole, fenbendazole, oxfendazole, oxibendazole, albendazole, albendazole sulfoxide, thiabendazole, thiophanate, febantel, netobimin, and/or triclabendazole or any combination thereof. The benzimidazoles generally have one or more substitutions of groups off of the benzene ring and/or the imidazole ring.

The anti-parasitic main mode of action of benzimidazole drugs is to impair the tubulin polymerization into microtubules, therefore disrupting microtubule-based processes.

Through a specially developed formulation, the present invention allows for the availability of these benzimidazole compounds essentially only after their excretion alongside feces, which can take place from about 10 hours to about 72 hours after ingestion (e.g., 12 hours to 72 hours, 20 hours to 72 hours, 30 hours to 72 hours, 40 hours to 72 hours), depending on the ruminant species that received the treatment. Therefore, there generally will not be any absorption of the active ingredient by treated animals, before the 10 hours to 72 hours. The composition containing benzimidazole compounds will be expelled from the ruminant organism through defecation. The delayed release or delayed availability of the active ingredient is due to the combining of the active ingredient with the other ingredients of the composition.

Therefore, generally, the active ingredient will be active only in the feces, sparing the animals from exposure to benzimidazole compounds. This delayed release mechanism avoids unwanted residues in milk or meat. Due to the present invention, the residue in the animal or milk of the animal after 10 hours to 72 hours of ingesting can be below 100 ppm or below 50 ppm or below 5 ppm or about 0 ppm, such as from 0 ppm to 1 ppm or 0 ppm. These ppm ranges are also applicable after 72 hours or more of ingesting the composition of the present invention.

Having the feces treated with the present invention's composition, and being that the feces practically are the only medium where helminth worms' eggs and larvae develop, particularly of the *Haemonchus* genre, and being that benzimidazole compounds have efficacy against eggs and larvae of helminths, the reproductive cycle of said parasites can be broken.

Delayed release of the benzimidazole compound or benzimidazole-containing compound means that the combination of ingredients used to form the composition of the present invention protects the benzimidazole from being activated, released or destroyed by gastric acids of the stomach(s) and avoids absorption in the intestine and/or other parts of the animal, so that the benzimidazole is present in the feces exiting the animal and then is released in the feces. For purposes of the present invention, the composition can be considered a targeted-release composition as the target of release is the feces. For purposes of the present invention, the composition can be considered an extended release composition in view of the 10 hour to 72 hour delay in the benzimidazole efficacy being activated.

With the elimination of eggs and larvae, the adult worms population will decrease, since there will be no immature larvae to develop into adults.

The composition of the present invention can include:
(a) at least one benzimidazole compound;
(b) at least one hydrophobic polymer (e.g., hydrophobic binding polymer);
(c) at least one hydrophilic polymer; and
(d) at least one particulate solid carrier.

Examples of benzimidazole compounds or benzimidazole containing compounds are thiabendazole, fenbendazole, albendazole, triclabendazole, cambendazole, parbendazole, mebendazole, flubendazole, oxfendazole, carbendazin, fuberidazole, triazoxide, ricobendazole, oxibendazole, and/or one of its derivatives or salts thereof or prodrugs thereof. Most preferably, the benzimidazole compound is thiabendazole and/or fenbendazole and/or albendazole.

The amount of the active ingredient in the present invention's composition may vary according to the selected active ingredient. For example, the amount of the benzimidazole containing compounds can be from about 0.1% to about 30% in weight of benzimidazole compounds, based on the total weight of the composition. The wt % can be above 30 wt % if desired.

The at least one hydrophobic polymer for the present invention can be ethylcelulose, a zein, or a polymethacrylate copolymer, or any combination thereof. The hydrophobic polymer can be present in an amount of from 5 wt % to 55 wt %, based on the total weight of the composition, such as from 7.5 wt % to 30 wt % or from 10 wt % to 20 wt %.

The at least one hydrophilic polymer can be any hydrophilic polymer or polymers. The hydrophilic polymer can, as an option, be considered an adjuvant. The hydrophilic polymer in combination with the hydrophobic polymer preferably have the ability to achieve the delayed release of the active ingredient as described herein.

Examples of the hydrophilic polymer include, but are not limited to, hypromellose, polyvinylpyrrolidone, carragenine, hydroxipropilmethylcellulose, or any combination thereof.

The hydrophilic polymer can be present in an amount of from about 0 wt % or from 0 wt % to 40 wt %, based on the total weight of the composition, such as from 2.5 wt % to 30 wt % or from 5 wt % to 20 wt %.

The particulate solid carrier can be any commonly used carrier. Examples of the solid carrier include microcrystalline cellulose, calcium phosphate, calcium sulfate, mannitol, kaolin, or any combination thereof. The carrier can be present in an amount of from 20 wt % to 80 wt %, based on the total weight of the composition, such as from 30 wt % to 70 wt % or from 40 wt % to 65 wt %.

Additionally, the composition of the present invention may further include, if desired, one or more stabilizers, tensoactives, flavor enhancers, preservatives, and/or antioxidants. The composition can contain, as an option one or more diluents. Examples include starch, talcum powder, and/or calcium carbonate. The composition can contain one or more other ingredients as an option, such as a lubricant(s). An example of a lubricant is silicon dioxide. The composition can contain one or more pH adjustment agents or pH buffers, such as, but not limited to, an acid or base, such as, an organic simple acid. An example of a specific agent is ethyl citrate. The total amount of the optional ingredients can be, in total amounts (by wt % of the composition) of from about 0.1 wt % to about 10 wt %.

Generally, each of the components that form the composition of the present invention are in solid form, but this is not a requirement. The composition of the present invention can be prepared by mixing together each of the ingredients, for instance, in a tank to form a mixture that can be pelletized, granulated, or otherwise aggregated to form a whole host of sizes and/or shapes, such as spheres, rods, pellets, that can range in size from 3.5 mm to 0.05 mm or other sizes. When forming the composition by mixing the ingredients, a solvent can be used, such as an alcohol, like ethanol which can evaporate away. The composition can be a combination of dry ingredients, and if so, the composition can be considered a dry mix or a formulation. If one or more of the ingredients are liquid, the components can be mixed and so achieve a binding of the various ingredients. Generally, the mixture of components is a physical mixture where the components are homogenously distributed amongst each other.

When the composition is formed, it can be considered a matrix or agglomerate or aggregate.

The present invention further relates to a nematode controlling feed or feed supplement that comprises a) the composition of the present invention, as described herein, and b) a feed or a feed supplement. The feed and/or feed supplement can be mixed with the composition of the present invention or otherwise combined to form the nematode controlling feed or feed supplement.

Thus, the present invention also relates to a compound capable of controlling nematodes that use feces as a medium for their reproductive cycle, through the addition of said compound to feed or feed supplements offered to animals, in a quantity of the composition described above that is efficacious against such nematodes.

The feed to be offered to animals may be ground or pelletized. Nutritional supplementation can be selected—without limitations—from: sodium chloride, mineralized salt, calcium phosphate, vitamins concentrates, protein supplements, among others.

The present invention further relates to an auxiliary kit for controlling nematodes that use feces as a medium for their reproductive cycle, that comprises a canister containing the present invention's composition and a dosing device. The canister may have any capacity, but being particularly one that contains from about 100 g to 500 g, or 300 g of said composition, or a pail containing from 1 kg to 15 kg, or 6 kg of said composition. Particularly, the dosing device can dose up to 100 g of said compound according to the present invention's requirements.

In a particular realization, the kit may comprise usage instructions for said compound according to the present invention's requirements.

The amount of said composition to be mixed with feed or feed supplement is to be established based on the estimated intake of the feed or feed supplement in use, which, in livestock operations, is common knowledge.

For purposes of the present invention, the controlling of eggs and larvae, or the controlling of eggs and larvae of a helminth or helminths means that the eggs and larvae are substantially or completely killed in the feces due to the composition of the present invention. The kill rate can be over a 90% kill rate based on the nematode or egg or larvae population of helminth in the feces, or over a 95% kill rate, or over a 98% kill rate, or about a 100% kill rate or a 100% kill rate of the eggs and larvae.

As an example, the dosage of the composition of the present invention to an animal can be from about 50 mg to 125 mg of active ingredient/animal/day or from about 60 mg to 100 mg, or from about 70 mg to 80 mg of active ingredient/animal/day. If included in a feed or feed supplement, the composition can be present in an amount to achieve this dosage range.

By way of illustration, the following quantities can be added to feed or feed supplement to achieve the desired dosage range with about 2 wt % of active ingredient present:

a) for feed supplement with daily intake between 60-120 g per head, 66 g to 80 g of the present invention's composition are to be mixed with each 1 kg of the feed supplement.

b) for feed with daily intake between 3-6 kg per head, 1350 g to 1620 g of the present invention's composition are to be mixed with each 1,000 kg of the feed.

Presented below are further examples of particular formulations of the present invention, with no limitations whatsoever to its scope besides those contained in the attached claims.

Examples of compositions for 1 kg of product:

Example 1—Compositions Containing Benzimidazole Compounds

Example 1A

| Components | Quantity |
| --- | --- |
| Thiabendazole | 20 g |
| Ethyl Acrylate Copolymer, Methyl metacrilate and trimethylammonium ethyl methacrylate chloride - | 550 g |

-continued

| Components | Quantity |
| --- | --- |
| Eudragit RS - CAS [33434-24-1] | |
| Triethyl citrate | 25 g |
| Microcrystalline Cellulose | 405 g |

Example 1B

| Components | Quantity |
| --- | --- |
| Fenbendazole | 100 g |
| Ethyl Acrylate Copolymer and Methyl metacrilate 2:1 - Eudragit NM - [9010-88-2] | 300 g |
| Triethyl citrate | 10 g |
| Calcium Phosphate | 590 g |

Example 1C

| Components | Quantity |
| --- | --- |
| Fenbendazole | 100 g |
| Ethyl Acrylate Copolymer and Methyl metacrilate 2:1 - Eudragit NM - [9010-88-2] | 250 g |
| Triethyl citrate | 10 g |
| Cellulose | 200 g |
| Kaolin | 440 g |

Example 1D

| Components | Quantity |
| --- | --- |
| Albendazole | 100 g |
| Ethyl Acrylate Copolymer and Methyl metacrilate 2:1 - Eudragit NE - [9010-88-2] | 150 g |
| Triethyl Citrate | 10 g |
| Calcium Phosphate | 290 g |
| Microcrystalline cellulose | 450 g |

Example 1E

| Components | Quantity |
| --- | --- |
| Thiabendazole | 20 g |
| Zein | 400 g |
| Starch | 40 g |
| Microcrystalline cellulose | 300 g |
| Kaolin | 240 g |

Example 1F

| Components | Quantity |
| --- | --- |
| Fenbendazole | 100 g |
| Ethylcellulose | 100 g |
| Hypromellose | 50 g |

-continued

| Components | Quantity |
| --- | --- |
| Microcrystalline cellulose | 200 g |
| Kaolin | 550 g |

Example 1G

| Components | Quantity |
| --- | --- |
| Albendazole | 100 g |
| Ethylcellulose | 150 g |
| Carragenine | 200 g |
| Calcium carbonate | 100 g |
| Calicum Phosphate | 450 g |

Example 1H

| Components | Quantity |
| --- | --- |
| Thiabendazole | 200 g |
| Ethylcellulose | 50 g |
| Hypromellose | 400 g |
| Sodium lauryl ether sulfate | 20 g |
| Microcrystalline cellulose | 330 g |

Example 1I

| Components | Quantity |
| --- | --- |
| Fenbendazol | 100 g |
| Ethyl Acrylate Copolymer and Methyl metacrilate 2:1 - Eudragit NM - [9010-88-2] | 300 g |
| Triethyl Citrate | 15 g |
| Microcrystalline cellulose | 135 g |
| Kaolin | 450 g |

Example 1J

| Components | Quantity |
| --- | --- |
| Albendazole | 100 g |
| Zein | 400 g |
| Starch | 40 g |
| Microcrystalline cellulose | 460 g |

Example 1K

| Components | Quantity |
| --- | --- |
| Thiabendazole | 20 g |
| Zein | 300 g |
| Starch | 50 g |
| Microcrystalline cellulose | 500 g |
| Calcium sulfate | 130 g |

Example 1L

| Components | Quantity |
| --- | --- |
| Fenbendazole | 100 g |
| Zein | 350 g |
| Polyvinylpyrrolidone | 30 g |
| Microcrystalline cellulose | 170 g |
| Kaolin | 350 g |

Example 1M

| Components | Quantity |
| --- | --- |
| Albendazole | 300 g |
| Ethylcellulose | 50 g |
| Hypromellose | 350 g |
| Sodium Lauryl Benzene Sulfonate | 30 g |
| Kaolin | 270 g |

Example 1N

| Components | Quantity |
| --- | --- |
| Thiabendazole | 20 g |
| Ethylcellulose | 150 g |
| Hypromellose | 50 g |
| Silicon dioxide | 40 g |
| Microcrystalline cellulose | 740 g |

Example 1O

| Components | Quantity |
| --- | --- |
| Fenbendazole | 100 g |
| Ethylcellulose | 200 g |
| Hypromellose | 50 g |
| Silicon dioxide | 50 g |
| Microcrystalline cellulose | 600 g |

The present invention includes the following aspects/embodiments/features in any order and/or in any combination:

1. A composition for the control of eggs and larvae of a helminth that develops in ruminant feces, comprising:
   (a) at least one benzimidazole compound;
   (b) at least one hydrophobic polymer;
   (c) at least one particulate solid carrier, and
   (d) optionally, at least one hydrophilic polymer.
2. The method of any preceding or following embodiment/feature/aspect, wherein said helminth is of the *Haemonchus* genre, and the ruminant feces is from the suborder of Ruminantia.
3. The method of any preceding or following embodiment/feature/aspect, wherein the benzimidazole compound is thiabendazole, fenbendazole, albendazole, triclabendazole, cambendazole, parbendazole, mebendazole, flubendazole, oxfendazole, carbendazim, fuberidazole, triazoxide, ricobendazole, oxilbendazole, or a derivative thereof, or any combination thereof.
4. The method of any preceding or following embodiment/feature/aspect, wherein the benzimidazole compound is thiabendazole, fenbendazole, or albendazole, or any combination thereof.
5. The method of any preceding or following embodiment/feature/aspect, wherein the hydrophobic polymer is ethylcellulose, zein, a methyl methacrylate copolymer, or any combination thereof.
6. The method of any preceding or following embodiment/feature/aspect, wherein the hydrophilic polymer is present.
7. The method of any preceding or following embodiment/feature/aspect, wherein the particulate solid carrier is microcrystalline cellulose, calcium phosphate, calcium sulfate, mannitol, kaolin, or any combination thereof.
8. The method of any preceding or following embodiment/feature/aspect, further comprising a stabilizer, a flavoring agent, a flavor enhancer, a preservative, a tensoactive, a lubricant, a diluent, a lubricant, a pH adjustment agent, or an antioxidant, or any combination thereof.
9. A feed or feed supplement composition comprising a) feed or feed supplement offered to animals and b) an efficacious amount of any preceding or following embodiment/feature/aspect.
10. The feed or feed supplement composition of any preceding or following embodiment/feature/aspect, wherein the feed is ground or pelletized.
11. The feed or feed supplement composition of any preceding or following embodiment/feature/aspect, wherein the feed supplement is sodium chloride, mineralized salt, calcium phosphate, a vitamin concentrate, a protein supplement, or any combination thereof.
12. A kit for controlling nematodes that develop in ruminant's feces comprising a canister containing the composition of any preceding or following embodiment/feature/aspect and a dosing device.
13. The kit of any preceding or following embodiment/feature/aspect further comprising written instructions for its use.
14. The kit of any preceding or following embodiment/feature/aspect, wherein the canister contains about 300 g of said composition and a 25 g-dosing device for dosing of said composition.
15. The kit of any preceding or following embodiment/feature/aspect, wherein said canister is a pail containing about 6 kg of said composition and a 25 g-dosing device for dosing of said composition.
16. A method to control eggs and larvae of helminths present in ruminants' feces, said method comprising administering to an animal, by oral route, through means of feed or feed supplement, the composition of any preceding or following embodiment/feature/aspect.
17. The method of any preceding or following embodiment/feature/aspect, wherein said method enhances zootechnical performance of ruminants by means of controlling eggs and infective larvae in their habitat.
18. The composition of any preceding or following embodiment/feature/aspect, wherein said benzimidazole compound is present in an amount of from 0.1 wt % to about 20 wt %, based on the total weight of said composition.
19. The composition of any preceding or following embodiment/feature/aspect, wherein said benzimidazole compound is present in an amount of from 0.1 wt % to about 20 wt %, said hydrophobic polymer is present in an amount of from about 5 wt % to about 55 wt %, said hydrophilic polymer is present in an amount of from 0 wt % to about 40 wt % and said particulate solid carrier is present in an amount of from 40 wt % to about 75 wt %, based on a total weight of said composition.

20. The method of any preceding or following embodiment/feature/aspect, wherein said composition is administered to said animal in an amount of from about 4 g to about 8 g.

21. The composition of any preceding or following embodiment/feature/aspect, wherein said benzimidazole compound in said composition is bioactively released on a delayed release basis.

22. The composition of any preceding or following embodiment/feature/aspect, wherein said delayed release is from about 10 hours to 72 hours from consumption of the composition by an animal.

23. The method of any preceding or following embodiment/feature/aspect, wherein said composition is delayed released with respect to said benzimidazole compound such that the release occurs in the feces of said ruminant.

24. The method of any preceding or following embodiment/feature/aspect, wherein said animal after 10 hours to 72 hours has a residue of said benzimidazole compound of less than 100 ppm.

25. The method of any preceding or following embodiment/feature/aspect, wherein said animal after 10 hours to 72 hours has a residue of said benzimidazole compound of less than 1 ppm.

26. The composition of any preceding or following embodiment/feature/aspect, wherein said hydrophilic polymer is present and is hypromellose, polyvinylpyrrolidone, carragenine, hydroxipropilmethylcellulose, or any combination thereof.

27. The composition of any preceding or following embodiment/feature/aspect, wherein one or more of the following is additional present in the composition: starch, talcum powder, calcium carbonate, silicon dioxide, ethyl citrate, or any combination.

28. The composition of any preceding or following embodiment/feature/aspect, wherein said benzimidazole compound is present in an amount of from 0.1 wt % to about 20 wt %, said hydrophobic polymer is present in an amount of from about 5 wt % to about 55 wt %, said hydrophilic polymer is present in an amount of from 2.5 wt % to about 30 wt % and said particulate solid carrier is present in an amount of from 40 wt % to about 75 wt %, based on a total weight of said composition.

The present invention can include any combination of these various features or embodiments above and/or below as set forth in sentences and/or paragraphs. Any combination of disclosed features herein is considered part of the present invention and no limitation is intended with respect to combinable features.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the specification and practice of the invention disclosed herein. It is intended that the specification and examples be considered exemplary only, with a true scope and spirit of the invention being indicated by the following claims.

The invention claimed is:

1. A method to control eggs and larvae of helminths present in ruminants' feces, said method comprising administering to an animal, by oral route, through means of feed or feed supplement, the composition comprising:
    (a) at least one benzimidazole compound;
    (b) at least one hydrophobic polymer;
    (c) at least one particulate solid carrier, and
    (d) optionally, at least one hydrophilic polymer, wherein said composition is delayed released with respect to said benzimidazole compound such that the release occurs in the feces of said ruminant, and wherein said benzimidazole compound is present in an amount of from 0.1 wt % to about 20 wt %, said hydrophobic polymer is present in an amount of from about 5 wt % to about 55 wt %, said hydrophilic polymer is present in an amount of from 0 wt % to about 40 wt % and said particulate solid carrier is present in an amount of from 40 wt % to about 75 wt %, based on a total weight of said composition and the hydrophobic polymer is ethylcellulose, zein, a methyl methacrylate copolymer, or any combination thereof.

2. The method of claim 1, wherein said method enhances zootechnical performance of ruminants by means of controlling eggs and infective larvae in their habitat.

3. The method of claim 1, wherein said delayed release is from about 10 hours to 72 hours from consumption of the composition by an animal.

4. The method of claim 1, wherein said animal after 72 hours has a residue of said benzimidazole compound of less than 100 ppm.

5. The method of claim 1, wherein said animal after 72 hours has a residue of said benzimidazole compound of less than 1 ppm.

6. The method of claim 1, wherein said hydrophilic polymer is present and is hypromellose, polyvinylpyrrolidone, carragenine, hydroxipropilmethylcellulose, or any combination thereof.

7. The method of claim 1, wherein one or more of the following is additional present in the composition: starch, talcum powder, calcium carbonate, silicon dioxide, ethyl citrate, or any combination.

8. The method of claim 1, wherein said hydrophilic polymer is present in an amount of from 2.5 wt % to about 30 wt % based on a total weight of said composition.

9. The method of claim 1, wherein said helminth is of the *Haemonchus* genre, and the ruminants' feces is from the suborder of Ruminantia.

10. The method of claim 1, wherein the benzimidazole compound is thiabendazole, fenbendazole, albendazole, triclabendazole, cambendazole, parbendazole, mebendazole, flubendazole, oxfendazole, carbendazim, fuberidazole, triazoxide, ricobendazole, oxilbendazole, or a derivative thereof, or any combination thereof.

11. The method of claim 1, wherein the benzimidazole compound is thiabendazole, fenbendazole, or albendazole, or any combination thereof.

12. The method of claim 1, wherein the hydrophilic polymer is present.

13. The method of claim 1, wherein the particulate solid carrier is microcrystalline cellulose, calcium phosphate, calcium sulfate, mannitol, kaolin, or any combination thereof.

14. The method of claim 1, further comprising a stabilizer, a flavoring agent, a flavor enhancer, a preservative, a tensoactive, a lubricant, a diluent, a lubricant, a pH adjustment agent, or an antioxidant, or any combination thereof.

* * * * *